United States Patent [19]
Kvist

[11] Patent Number: 5,169,308
[45] Date of Patent: Dec. 8, 1992

[54] DEVICE FOR TOOTH IMPLANTATION

[75] Inventor: Björn Kvist, Norrtälje, Sweden

[73] Assignees: AB John Sjoding; Credentus AB, Nacka, Sweden

[21] Appl. No.: 631,445

[22] Filed: Dec. 21, 1990

[30] Foreign Application Priority Data

Dec. 22, 1989 [SE] Sweden .................. 8904340

[51] Int. Cl.$^5$ .............................................. A61C 8/00
[52] U.S. Cl. .................................. 433/173; 433/172
[58] Field of Search ............... 433/172, 173, 174, 175, 433/176, 220, 221

[56] References Cited

U.S. PATENT DOCUMENTS

| 583,565 | 6/1897 | Carr | 433/172 |
|---|---|---|---|
| 4,330,891 | 5/1982 | Branemark et al. | 128/92 G |
| 4,468,200 | 8/1984 | Munch | 433/174 |
| 4,758,161 | 7/1988 | Niznick | 433/173 |
| 4,863,383 | 9/1989 | Grafelmann | 433/174 |

FOREIGN PATENT DOCUMENTS

| 0216031 | 6/1986 | European Pat. Off. . | |
| 540713 | 3/1956 | Italy | 433/173 |
| 450335 | 6/1987 | Sweden . | |

OTHER PUBLICATIONS

"The Unique Method of Tissue Integration that Offers Patients New Quality of Life", Biotes.

Primary Examiner—John J. Wilson
Attorney, Agent, or Firm—Leydig, Voit & Mayer

[57] ABSTRACT

A device for tooth implantation having a fixture part intended to be set into the jawbone, and a holder part to which the tooth crown is attached. The holder part can be screwed on the fixture part by an attachment screw, and a locking screw is disposed to lock the attachment screw for fastening the holder part to the fixture part and prevent unscrewing.

9 Claims, 1 Drawing Sheet

DEVICE FOR TOOTH IMPLANTATION

BACKGROUND OF THE INVENTION

The present invention relates to a device for tooth implantation comprising a fixture part intended to be set into the jawbone, and a holder part to which the tooth crown is attached. The holder part can be and the fixture part can be coupled by an attachment screw.

SUMMARY OF THE INVENTION

The tooth implantation of the above mentioned type is successfully used for tooth bridges. When using this technique for single tooth implantation problems arise. The screw attaching the holder part carrying the tooth crown to the fixture part often becomes loose as a result of uneven loads on the tooth. When the tooth crown begins to get loose from the fixture part, the canal to the attachment screw must be bored, so that the screw can be tightened whereupon the canal is again filled. When the tooth crown is getting loose, there often also are increasing bacterial problems around the implantation. Because of these problems it has been very difficult to use the previously known technique of implantation for a single tooth.

The purpose of the present invention is to solve the above mentioned problem and provide a device for tooth implantation which makes a permanent locking of the implantation structure possible also for one-tooth implantation.

According to an advantageous aspect of the invention, the holder part presents a conical portion on which the tooth crown is mounted. If this portion is cylindric it will be difficult to move the crown down on the holder part to the intended fixation position. This can result in the formation of pockets between the crown and the gums after the implantation of the tooth with increasing bacterial problems as a consequence. These problems are thus solved by making the portion in question of the holder part conical. The optimum cone angle is 5°.

According to another aspect of the invention the cross section of the conical portion of the holder part is non circular, preferably quadrangular with rounded out corners or hexagonal, so that the tooth crown cannot turn on the holder part after being mounted.

BRIEF DESCRIPTION OF THE DRAWINGS

An embodiment of the device according to the invention will now be described more in detail with reference to the enclosed drawings

DETAILED DESCRIPTION OF EMBODIMENTS

Figure 1:
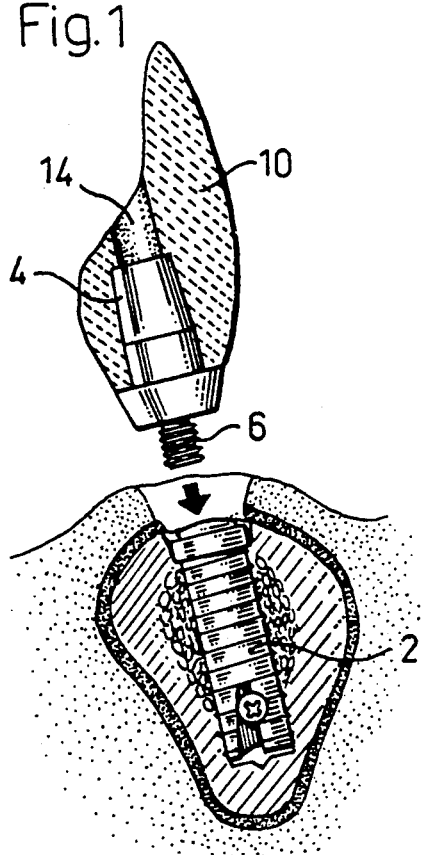
FIG. 1 shows the fixture part set in into the jawbone.

In FIG. 1 the fixture part is shown in the form of a threaded anchoring unit 2 made of titanium and set in the jawbone.

Figure 2:
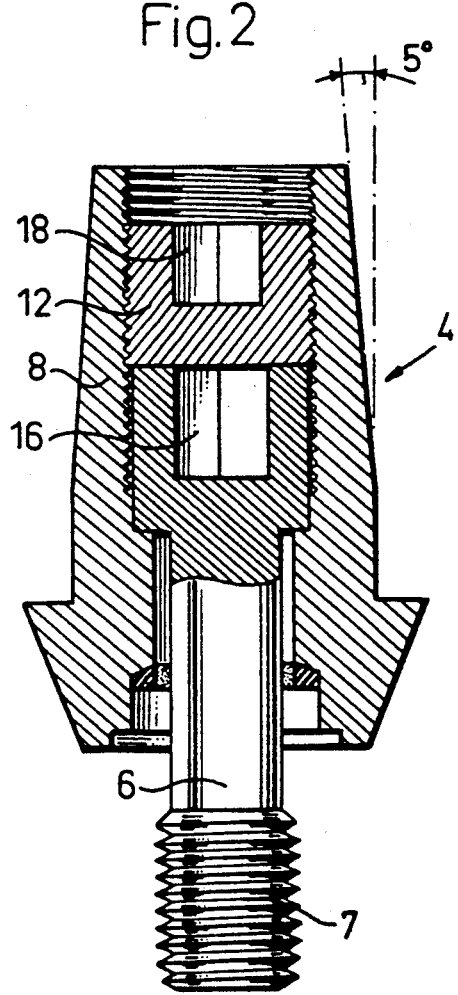
FIG. 2 depicts the holder part in enlarged scale including the attachment screw and the locking screw.

FIG. 2 discloses the holder part 4 which is intended to be screwed on the fixture part 2 by an attachment screw 6 located at the bottom region of the holder part, said attachment screw being threaded into a central bore in the fixture part 2.

The holder part 4 presents a conical portion 8 on which the tooth crown itself is intended to be attached by an adhesive, cement or porcelain burning. The cone portion 8 has a cone angle of between 5° and 15°. The optimum cone angle is 5° as depicted in FIG. 2.

As a consequence of uneven loads on the tooth crown when chewing the attachment screw 6 has, as mentioned above, a tendency to get loose and to prevent this a locking screw 12 is screwed into the bore against the attachment screw 6.

The attachment screw 6 includes a threaded end portion 7 which is screwed into the central bore of fixture part 2. The opposite end of attachment screw 6 is formed as a head portion 9.

Locking screw 12 is designed to be screwed into the bore of conical portion 8 to bear against head portion 9 of attachment screw 6. Locking screw 12 and threaded end portion 7 of attachment screw 6 are oppositely threaded so that when attachment screw 6 tends to unscrew locking screw 12 will become locked and secure attachment screw 6 in place. Ordinarily attachment screw 6 is a right-threaded screw while the locking screw 12 is a left-threaded screw and the bore of conical portion 8 is threaded to receive locking screw 12. Thus, the locking screw 12 will lock the attachment screw 6 if it would tend to unscrew.

In the upper portions of the screws there is a square recess 16 and 18 respectively, in which a matched screw tool can be inserted for tightening the screws. Of course the recesses can be of another shape e.g. of triangular or hexagonal shape.

The tooth crown 10 is mounted on the holder part 4 by a sterile procedure and the cross section of the conical section 8 is non-circular, e.g. quadrangular or hexagonal, so that rotation of the tooth crown 10 on the conical portion 8 is avoided.

The attachment screw 6 and the locking screw 12 are tightened through a canal 14 through the tooth crown 10, said canal 14 thereafter being filled up with a suitable filling material.

Figure 3:
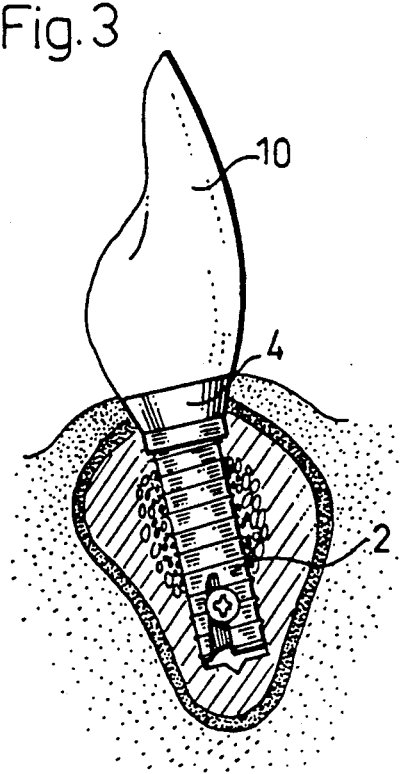
FIG. 3 illustrates a single tooth implantation.

A completed tooth implantation is illustrated in FIG. 3.

The invention is described above applied to a one-tooth implantation. Even if the problem with a loosening attachment screw, as mentioned above, is most severe for one-tooth implantations, also for bridges the attachment screws will have a tendency to get loose inspite of the fact that adjacent teeth will lock each other against movement. The invention can, however, also be used for implantation of tooth bridges to eliminate this problem also for such constructions. For bridges having a plurality of attachment screws, locking screws are not necessarily needed for locking each attachment screw, but it will be sufficient if at least some of the attachment screws are locked.

What is claimed is:

1. A device for tooth implantation comprising:
a fixture part having a threaded bore;
a holder part having a threaded bore;
a locking screw disposed in the threaded bore of said holder part;
an attachment screw having a head portion disposed in the threaded bore of said holder part contiguous to said locking screw, and a threaded end portion attachable to the threaded bore of said fixture part;
said locking screw and said attachment screw being oppositely threaded so that when said attachment screw tends to unscrew said locking screw locks and secures said attachment screw in place.

2. The device according to claim 1, wherein the attachment screw is right-threaded and the locking screw left-threaded.

3. The device according to claim 1 wherein the holder part includes a conical portion to which the tooth crown is attached.

4. The device according to claim 3, wherein the conical portion has a cone angle between 5° and 15°.

5. The device according to claim 4 wherein the cross section of the conical portion is non-circular.

6. The device according to claim 3 wherein the cross section of the conical portion is non-circular.

7. The device according to claim 6, wherein said cross section is quadrangular, preferably with rounded out corners.

8. The device according to claim 6, wherein said cross section is hexagonal, preferably with rounded out corners.

9. The device according to claim 1 further comprising a plurality of teeth forming a bridge secured to the fixture part by a plurality of screws, wherein the locking screws are disposed to lock at least some of the attachment screws.

* * * * *